United States Patent
Schmidt et al.

(10) Patent No.: US 6,500,615 B1
(45) Date of Patent: Dec. 31, 2002

(54) IDENTIFYING ANTISENSE OLIGONUCLEOTIDE BINDING

(75) Inventors: Günter Schmidt, Houghton (GB); Andrew Hugin Thompson, Alloway (GB)

(73) Assignee: Xzillion GmbH & Co., Frankfurt (DE)

( * ) Notice: Subject to any disclaimer, the term of this patent is extended or adjusted under 35 U.S.C. 154(b) by 0 days.

(21) Appl. No.: 09/269,555

(22) PCT Filed: Oct. 6, 1997

(86) PCT No.: PCT/GB97/02722

§ 371 (c)(1),
(2), (4) Date: May 26, 1999

(87) PCT Pub. No.: WO98/15651

PCT Pub. Date: Apr. 16, 1998

(30) Foreign Application Priority Data

Oct. 4, 1996 (GB) .............................................. 9620749

(51) Int. Cl.⁷ ............................ C12Q 1/68; C12P 19/34; C07H 21/04
(52) U.S. Cl. ............................ 435/6; 435/91.1; 536/24.5
(58) Field of Search ............................ 435/6, 7.1, 91.1, 435/91.3; 436/518; 536/23.1, 23.2, 24.5, 24.3, 24.33, 24.31; 514/44

(56) References Cited

FOREIGN PATENT DOCUMENTS

| EP | 0 614 988 A | 9/1994 |
|----|-------------|--------|
| WO | WO 91/08489 A | 6/1991 |
| WO | WO 95/21265 A | 8/1995 |
| WO | WO 97/10332 A | 3/1997 |

OTHER PUBLICATIONS

Mishra et al., Life Sciences, vol. 317, Nov. 94, pp. 977–982.
Cload et al., Journal of the American Chemical Society, vol. 116, No. 2, Jan. 26, 1994, pp. 437–442, XP000570388.
Ho et al., Nucleic Acids Research, vol. 24, No. 10, May 15, 1996, pp. 1901–1907, XP002006548.

*Primary Examiner*—Andrew Wang
*Assistant Examiner*—Karen A Lacourciere
(74) *Attorney, Agent, or Firm*—Burns, Doane, Swecker & Mathis, L.L.P.

(57) ABSTRACT

A method for identifying an antisense oligonucleotide capable of binding to a target mRNA, which comprises contacting the target mRNA with each member of an oligonucleotide library separately under hybridization conditions, removing unhybridized material and determining which member or members hybridize; wherein the oligonucleotide library comprises a plurality of distinct nucleotide sequences of a predetermined common length, and wherein each nucleotide sequence comprises a known sequence of 4 to 8 bases and all possible combinations of the known sequence are present in the library.

11 Claims, 10 Drawing Sheets

Figure 1:
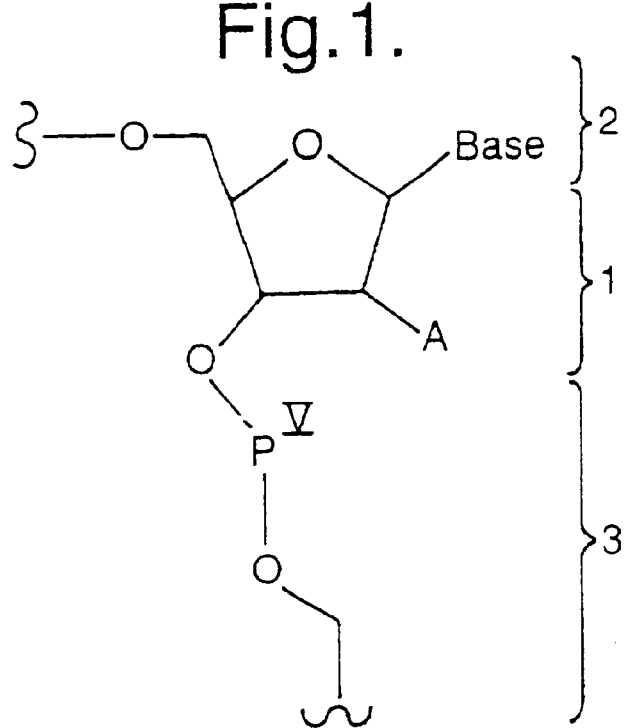
Figure 2:
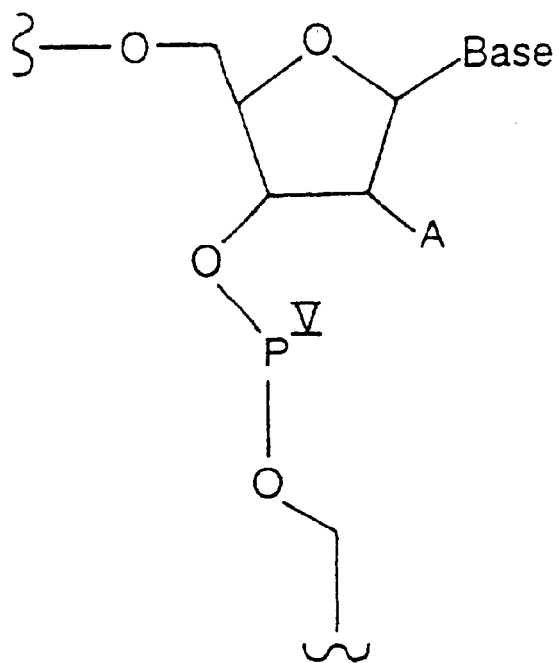
Figure 3:
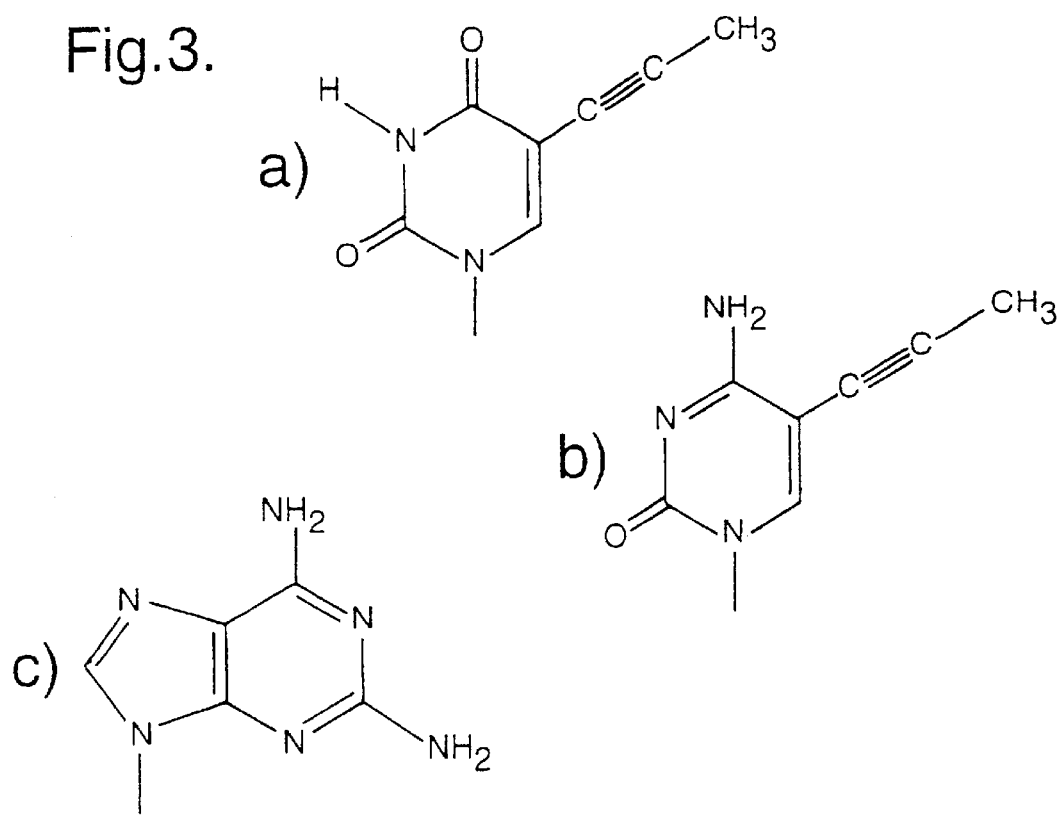
Figure 4:
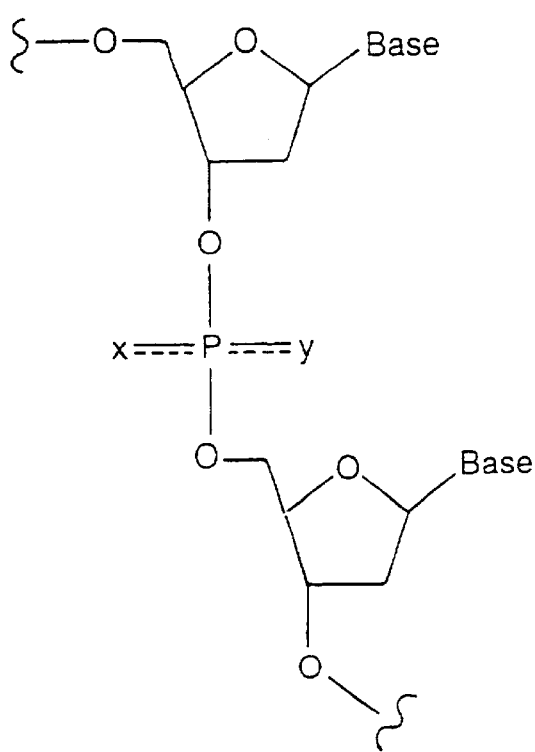
Figure 5:
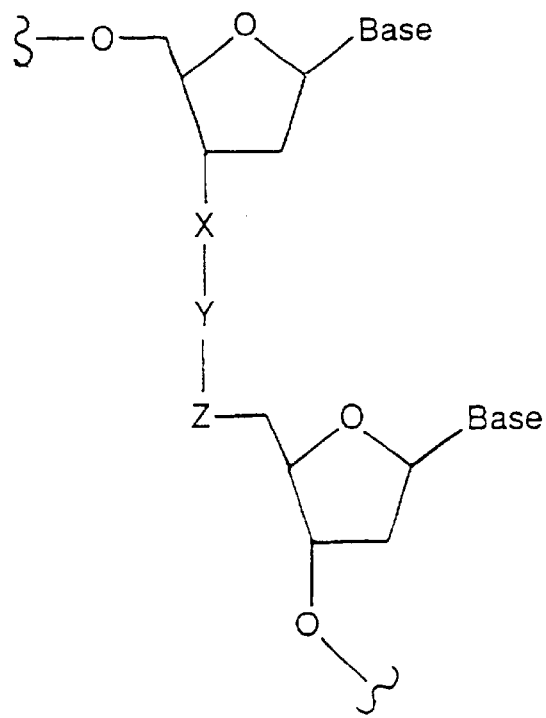
Figure 6:
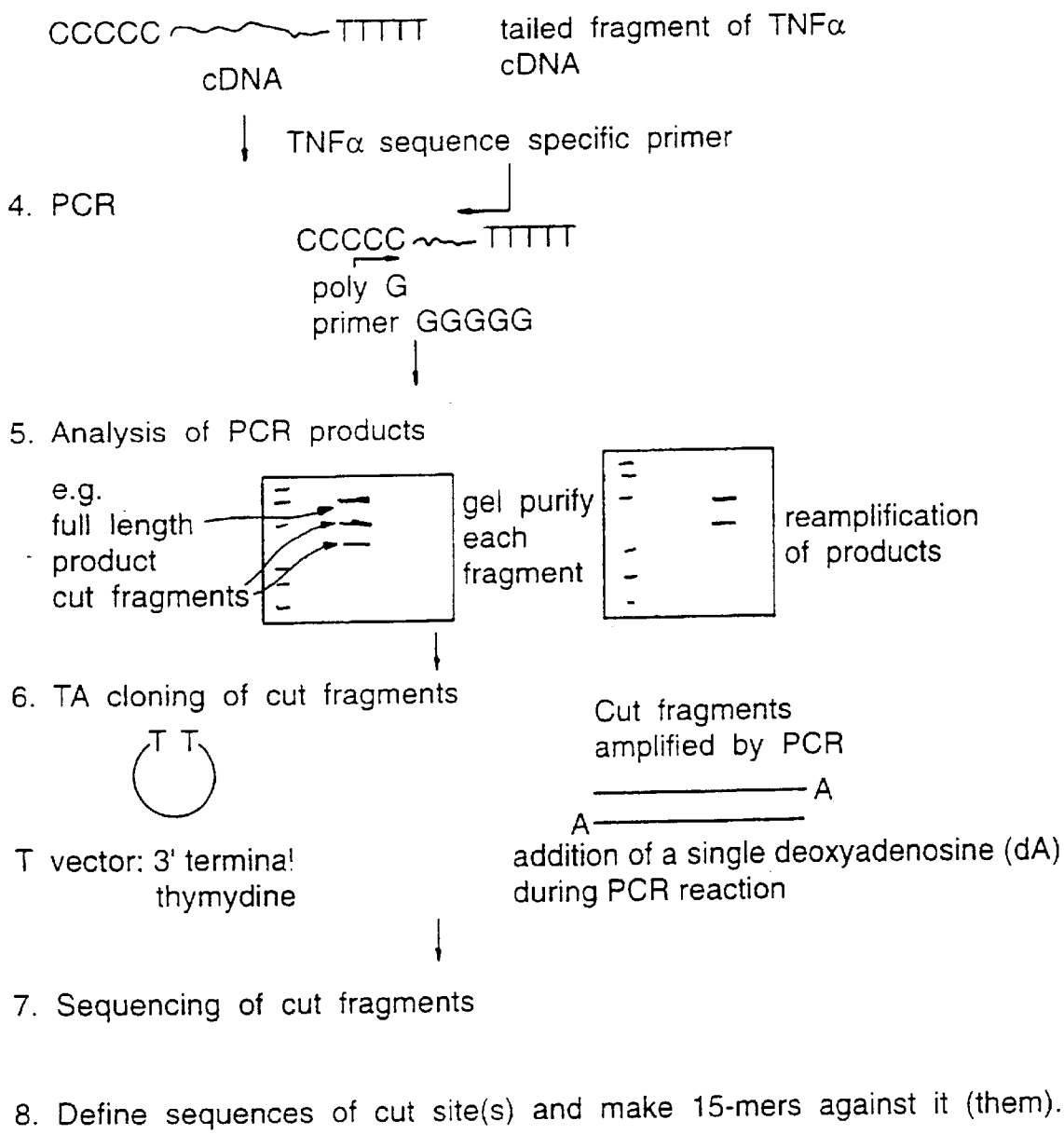
Figure 7A:
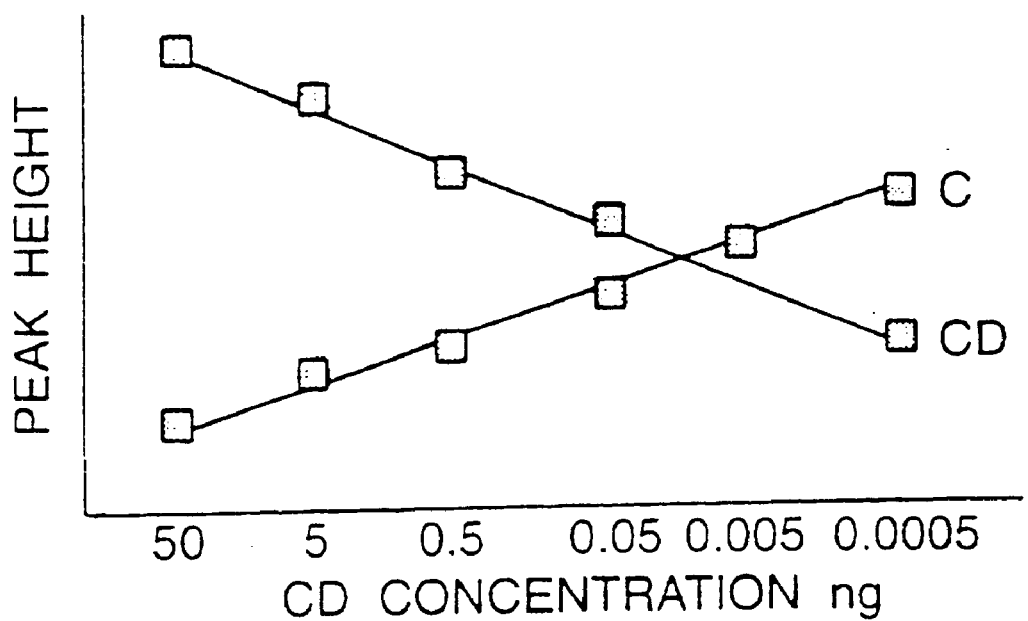
Figure 7B:
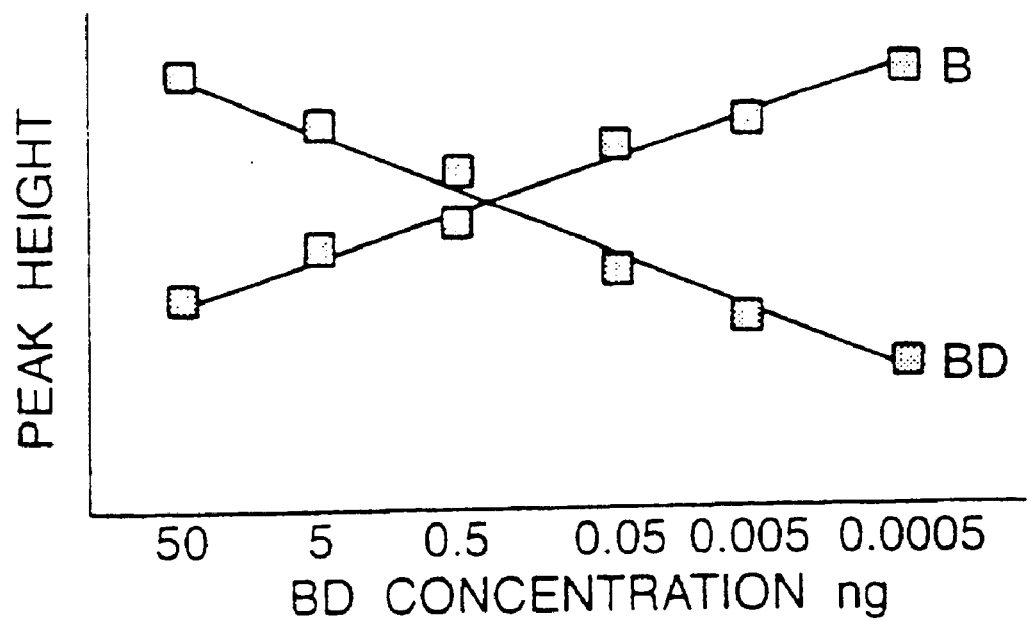
Figure 8:
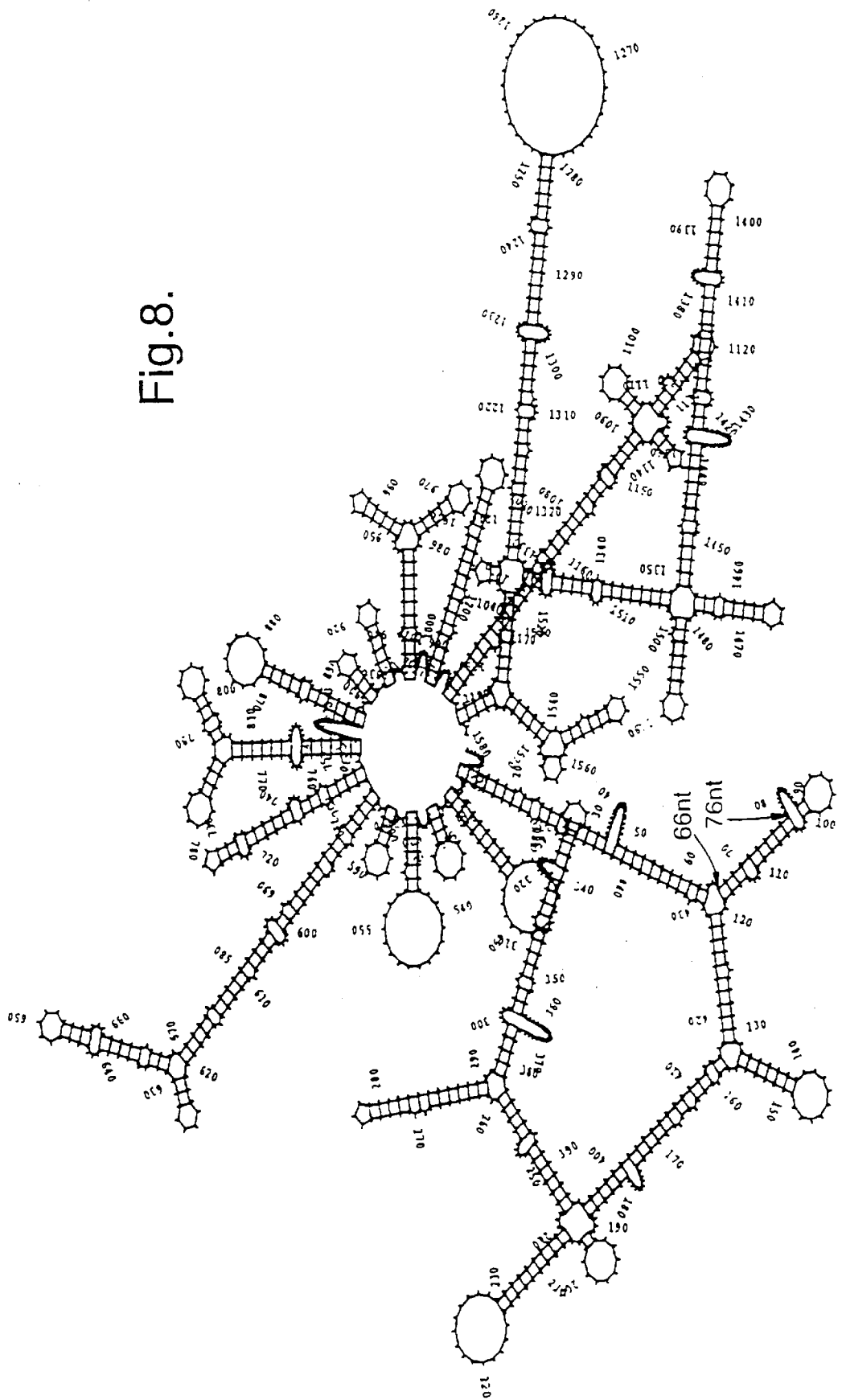
Figure 9:
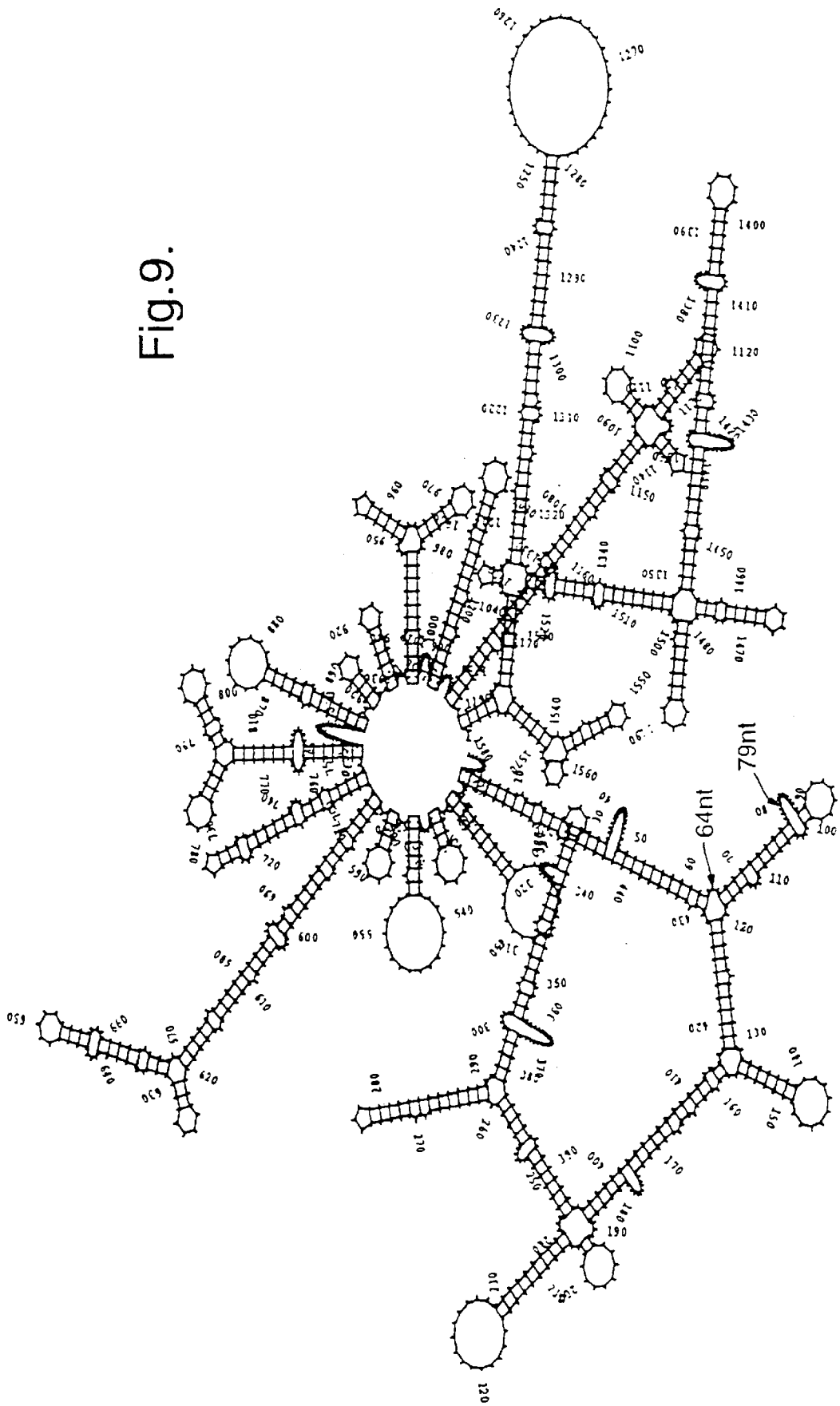
Figure 10:
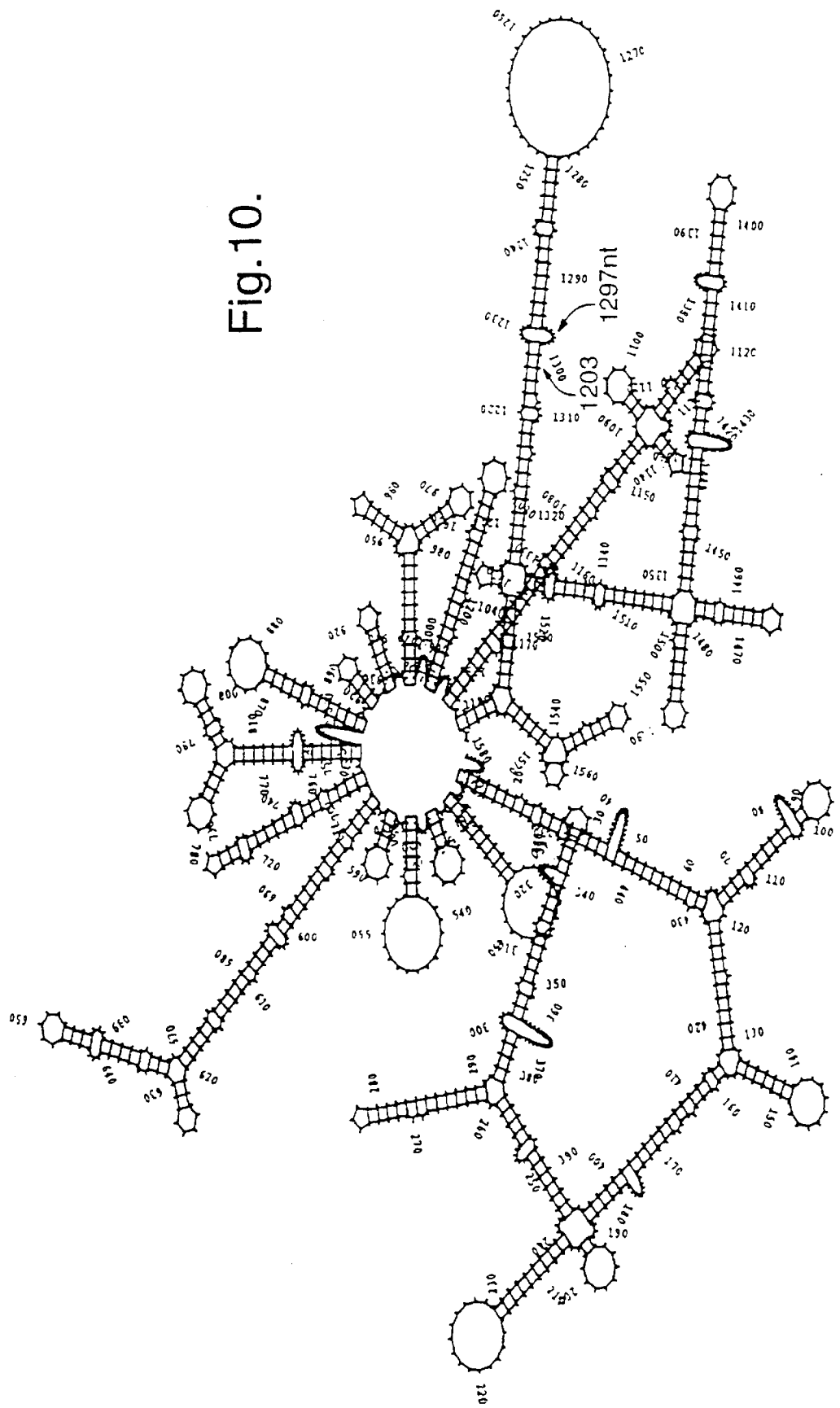
Figure 11:
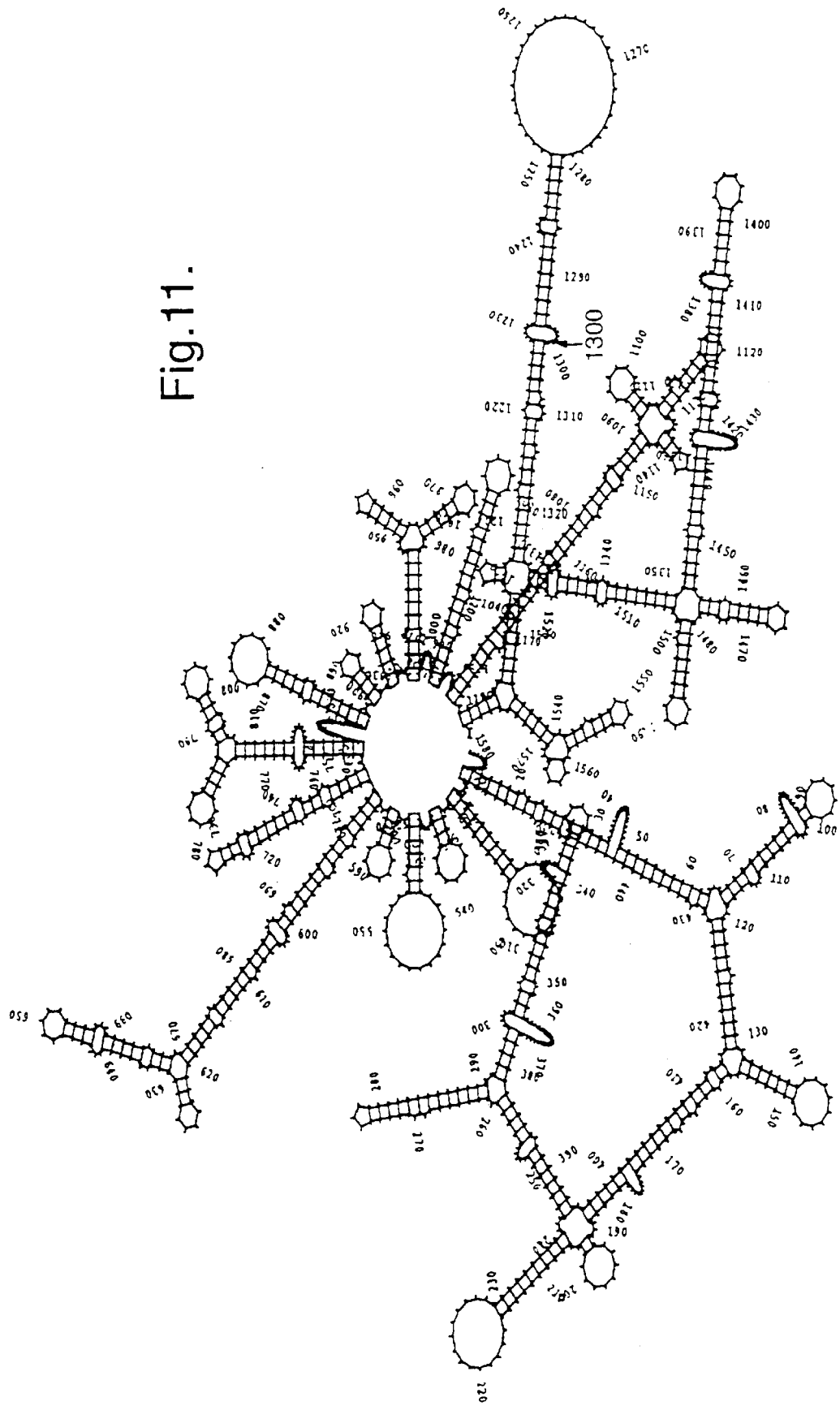
Figure 12:
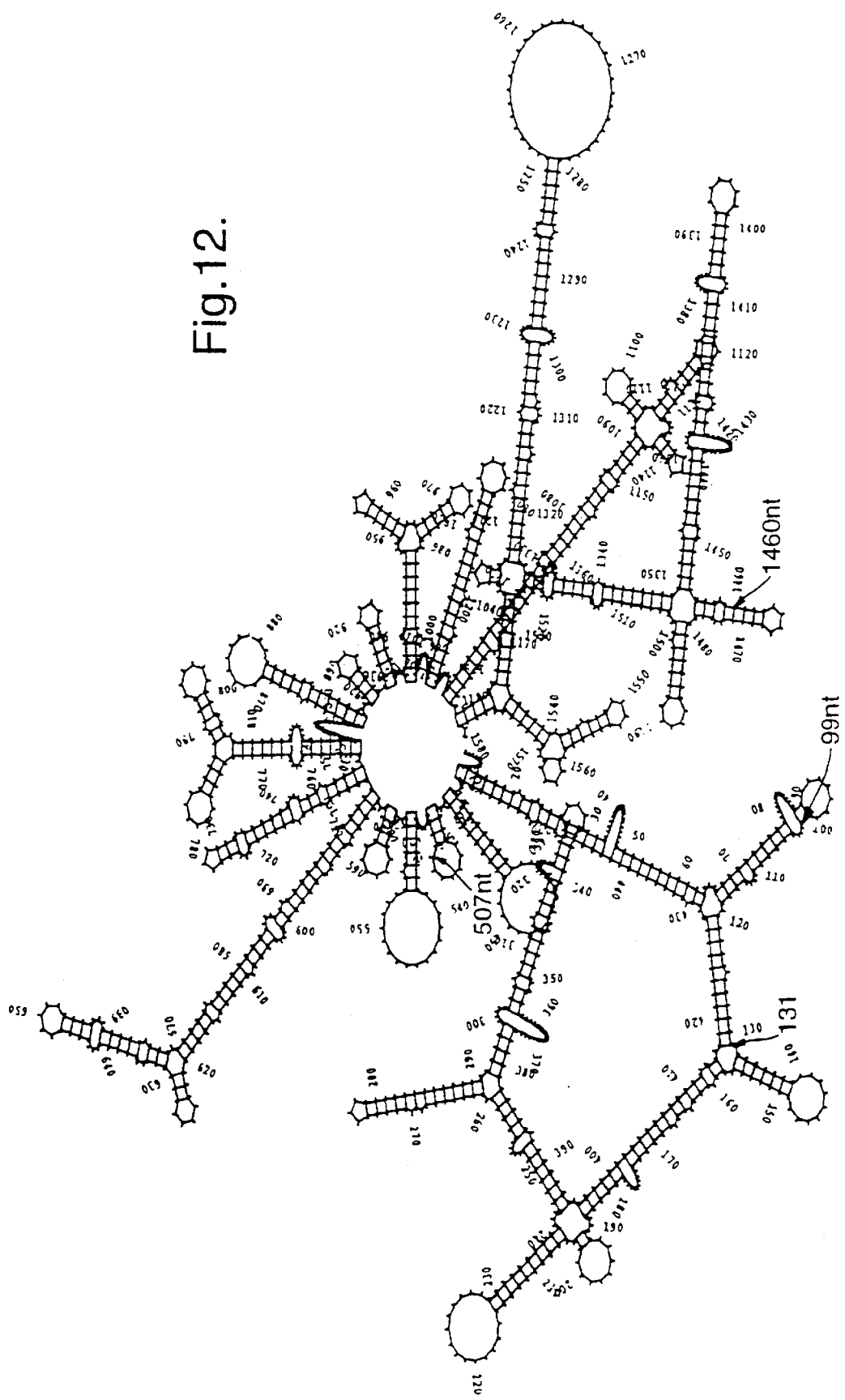

Fig.6.

target TNFα mRNA

Example ATG ———————┬————————————┬———————— AAAAA
                  cut          cut
                  site         site 1. CAOs   NNNNNnnnnnNNNNN :(15-mer)

Yield
99.8%   ATG ——————— TNFα mRNA ———— · · · ———— AAAAA   full length mRNA (not cut)

cut site 1
0.15%   ATG ——————              ———— · · · —AAAAA    cut species 1
          NNNNNnn   nnnNNNNN                         (mRNA fragment)

cut site 2
0.05%   ATG ——————              ———— · · · AAAAA     cut species 2
          NNNNnnn   nnNNNN                           (mRNA fragment)

2. RT-PCR synthesis of 1st cDNA strand:

ATG ————————————————— AAAAA  ← mRNA
         ~~~~~~~   TTTTT  ← fragment
          cDNA            poly T primer Denature (Heat/NaOH)

3.              cDNA
         ~~~~~~~~~~~ TTTTT      1st cDNA strand
              +
tailing of cut site: TdT and dCTP
                       or
                     (d dGTP)

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:3'
      biotinylated oligo (cap 53B)

<400> SEQUENCE: 1
ccactagttc tagagcggcc gccaccgcgg                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:5'
      biotinylated oligo (cap 35B)

<400> SEQUENCE: 2
ccccccctcg aggtcgacgg tatcgataag                                    30

↓

IDENTIFYING ANTISENSE OLIGONUCLEOTIDE BINDING

FIELD OF THE INVENTION

The present invention relates to a method for identifying accessible sites in an RNA molecule for antisense agents and to methods for identifying antisense oligonucleotides.

BACKGROUND TO THE INVENTION

Most library strategies used for identifying oligonucleotides (ONs) that bind an RNA have relied on cleavage of the target mRNA by RNAse H as the key component of their selection process. This, however, only selects for ONs which bind their targets with normal Watson-Crick interactions. ONs that bind their target RNA can mediate cleavage by RNAse H and the resultant fragments can be isolated by high resolution gel electrophoresis. The precise sequence of the successful ON is determined by sequencing the fragments. Mishra and Toulmé (1) have developed an alternative selection procedure based on selective amplification of ODNs (Oligodeoxynucleotides) that bind their target and have demonstrated non-Watson-Crick interactions in that binding. Their protocol requires just as much sequencing as the RNAse H strategy but they sequence the ODNs and not the target RNA fragments. Furthermore most library strategies use libraries that are free in solution which has the problem of cross hybridisation of ONs within the library. This can be solved by using mulitple libraries of minimally cross hybridising subsets but this adds to the labour involved in the selection of ODNs with active antisense properties.

SUMMARY OF THE INVENTION

The present invention provides a method for identifying an antisense oligonucleotide capable of binding to a target mRNA, which comprises contacting the target mRNA with each member of an oligonucleotide library separately under hybridisation conditions, removing unhybridised material and determining which member or members hybridise; wherein the oligonucleotide library comprises a plurality of distinct nucleotide sequences of a predetermined common length, and wherein each nucleotide sequence comprises a known sequence of 4 to 8 bases and all possible combinations of the known sequence are present in the library.

Each member of the oligonucleotide library may be contacted with the target mRNA in a separate container which may be immobilised in the container. Alternatively, each member of the oligonucleotide library may be immobilised at a separate location on a hybridisation array. Preferably the length of the known sequence is from 4 to 6 bases.

Each member of the oligonucleotide library may comprise a set of nucleotide sequences. Each nucleotide sequence may have a window region comprising the known sequence and a flanking region of no more than 8 bases, wherein all possible combinations of bases in the flanking region are present in each set and the common length of the nucleotide sequences is no more than 12 bases, preferably no more than 10 bases. The nucleotide sequences may be made from DNA analogues.

In one arrangement, the step of determining which member or members hybridises comprises determining the member or members which hybridise more rapidly.

The sequence of each member which hybridises may be compared with sequence information relating to the target mRNA so as to identify in the target mRNA one or more antisense binding sites.

DESCRIPTION OF THE PREFERRED EMBODIMENTS

This invention is aimed at the problem of identifying accessible sites within an mRNA but the object of this technique is to find accessible sites in a system that is applicable to any RNA molecule, that requires no sequencing and is not biased by the use of RNAse H. The emphasis of this patent is on the use of libraries of short oligonucleotide (ON) probes, preferably 4-mers. This invention provides a method for determining the accessible sites of an RNA to short ON probes by following the hybridisation reactions of each of the probes in the library with the target. Probes are spatially isolated and in the reactions, and either the probe or the target RNA is immobilised.

The rationale behind using probes with windows as short as 4mers is the assumption that most occurrences of a given 4-mer will be sequestered in secondary or tertiary structure. The data gained from following each individual hybridisation is interpreted in terms of the primary sequence:— hybridisation of several 4 mers to an accessible region will be marked by clustering of overlapping 4-mers in the primary sequence of the RNA. Ambiguities should be resolvable in part by analysis of the binding kinetics, so even if a 4-mer occurs more than once, it should still be possible in most cases to identify the most accessible regions in the RNA. The importance of using short probes is the ability to calibrate and normalise the hybridisation behaviour of all members of the library, since the library is not so large that this is impractical. A 4-mer library has 256 members, which is a modest number and it is realistic to test such a library against a number of model molecules to calibrate the system. Calibration is important as most 4-mers have different binding energies for a given degree of accessibility. In order to identify the regions of a molecule that are accessible on the basis of hybridisation kinetics requires that one be able to compare normalised kinetic data that takes into account that discrete overlapping 4-mers will bind the same accessible site with different kinetics. Small arrays of probes are cheaper to construct and manipulate when spatial isolation of probes is desired. Furthermore short probes are much less likely to have any secondary or tertiary structure themselves which would complicate the analysis of the hybridisation reactions.

Hybridisation times can be varied to derive kinetic data about each hybridisation reaction. The amount of probe ON hybridised after a given time will give quantitative data about the binding affinity of that probe for its target. By varying the hybridisation duration, a time course for the hybridisation reaction of each probe can be derived. The accessibility of any region of the structure will be inversely related to the time its complementary probe will take to bind hence detailed information about secondary structure can be acquired by this approach. In combination with a Scintillation Proximity Assay (Amersham), discussed below, the system is still more effective in that no washing is needed, so shorter probes can be used and the hybridisation reaction of each probe can be followed in real time.

Molecular Probes of RNA Structure

Spatial isolation and immobilisation of probes avoids cross-hybridisation problems associated with the use of oligonucleotide libraries free in solution simplifying interpretation of results. This process does not necessarily determine the most effective cut sites for RNAse H but provides detailed structural information about the target RNA to allow rational design of targetted molecules which can be then be developed into effective antisense agents, which will not necessarily operate on the basis of RNAse H mediated RNA degradation.

Advantages Over Previous Library Strategies

This invention uses random libraries of ONs since, in a random library of ONs of a given length, every possible sequence of that length is represented, hence every sub-sequence of that length that comprises a given target RNA is also represented. This means that a random library will be applicable to any RNA and will contain all the target subsequences within it. Since ONs are monitored independently, this means that this approach entails the targeted libraries discussed in a previous patent PCT/GB96/02275, and gives detailed kinetic behaviour about them. Explicit data concerning accessibility of sub-regions of the RNA to normal Watson-Crick interactions can thus be derived by this system.

Non-Watson-Crick interactions might well be less common than the normal complementary interactions but will also be represented in a system like this. One would expect interactions with regions that are partially complementary to the target RNA. If Watson-Crick interactions are the only potential interactions that are possible, such partial hybridisation would be expected to be weak but if non-Watson-Crick interactions play a role, as Mishra and Toulmé suggest (1), then subsets of these interactions might be expected to have higher strength interactions with the target RNA. Hence this strategy will identify potentially specific interactions that are non-Watson-Crick.

There appears to be a difference in the results of experiments performed with random libraries and those with targeted libraries. Different cut sites were identified by each library in the experiments performed in our previous patent application PCT/GB96/02275. In those experiments the targeted libraries covered only three specific sub-regions of the target RNA, TNFa. However the sites identified by this library were not identified by the random library. This is probably due to the fact that targeted libraries have fewer members, each of which are at higher relative concentrations than might be the case for members of a random library. The random library, therefore, picked up more accessible sites in regions not covered by the targeted libraries but the ONs corresponding to those used in the targeted library did not pick up the same cut sites. The cut sites picked up by the targeted libraries may have been due to their relatively higher concentration so these may not have been the most accessible. The problem of cross-hybridisation is also difficult to assess in these systems and the contribution of this effect is likely to be different for each type of library. This novel approach should normalise all of these effects giving much more meaningful data.

Kinetic data should also be acquired by this approach, as discussed below, which will give detailed structural information about target RNAs.

Kinetic Data from Hybridisation Experiments

Hybridisation times can be varied to derive kinetic data about each hybridisation reaction. The amount of probe ON hybridised after a given time will give quantitative data about the binding affinity of that probe for its target. By varying the hybridisation duration, a time course for the hybridisation reaction can be derived. The accessibility of any region of the structure will be inversely related to the time its complementary probe will take to bind to a given degree hence detailed information about secondary structure should be acquired by this approach.

This procedure would be impossible if libraries of large ONs were used due to the number of ONs that would be required. Calibration of each of the probes in a large library would be a massive task, although with automated image analysis of combinatorially synthesised chips, it might be feasible. However it is not necessary or desirable to use large oligonucleotides.

Real Time Kinetic Assays

Radiolabelling is a favourable labelling scheme with desirable properties, particularly radio-isotopes that produce low energy radiation with short path lengths such as $^{33}$p. Radiolabelling permits the development of proximity assays. The radiation emitted can be detected by various means, including scintillation or by geiger counters. Proximity detection systems and corresponding proximity assays measure the intensity of a signal from a label which gives a measure of the distance of the label from the detector. Scintillation proximity assays for example are based on the detection of radiation emitted from a radio-isotope. The amount of radiation reaching a scintillant surface is detected by photo-amplification of the scintillation. The mean path length of certain forms of radiation is fairly short. Beta radiation from $^{33}$P has a relatively low energy and short path length. This means a probe labelled with $^{33}$P will be detected only when it is relatively close to the detection surface. The further from the source the lower the intensity that is measured.

If an RNA molecule is labelled with $^{33}$P, and hybridised to an oligonucleotide probe immobilised on a scintillant containing surface or visa versa, one would expect the scintillation count to increase as the amount of RNA hybridised to the probe increases. One would expect there to be a background count, from molecules free in solution close enough to the scintillant surface to be detected, so control reactions with labelled RNA or probe depending on which is to be labelled in the actual assays must be performed. In this sort of system, spatial resolution of probes is essential, as only one radiolabel can be used at a time, so only one probe or RNA could be labelled at a time. The primary benefit of a system based on radiolabelling is the ability to measure hybridisation reactions in real time to give detailed kinetic data. Real time analysis can be achieved by detecting scintillation with a photoamplification and detection system coupled to appropriate signal processing electronics such as the Amersham Cytostar-T scintilling microplates.

Hybridisation Probes

There are two complementary difficulties with the use of short ON libraries. To ensure that the hybridisation of probe to an immobilised RNA is strong enough, one requires that the oligonucleotides be long enough to ensure a reasonable degree of hybridisation but the longer the probe the more massive the task of resolving the behaviour of individual library members. Since RNA/DNA hybrids have higher binding energies than RNA/RNA or DNA/DNA duplexes they are more stable than either of the homo-duplexes, one can use shorter probes than one might use for homogenous interactions and one can use non-natural analogues that have higher binding affinity for natural nucleic acids than probes composed of natural nucleic acids.

Non-Natural Nucleic Acid Analogues

Since this approach does not require recognition by RNAse H, one has more flexibility in the use of non-natural backbones. One can use non-natural base analogues to increase binding energies of any interactions. For the purposes of this system one might use a backbone that is less charged than the natural phosphodiester linkages such as methylphosphonodiester linkages or peptide nucleic acids, Increased energies of probe binding interactions might be useful to allow strand invasion of double stranded regions more easily by the immobilised probed oligonucleotides, the kinetics of which should reveal useful information about the structure of the region being invaded.

Increasing 'Bound' Time of ON Probes

The problem of weak hybridisation that faces this embodiment is quite acute in the light of the fact that the shorter the ON, the more readily the molecule will dissociate from its target RNA. In carrying out structural probes using short ONs, a large quantity of the probe oligonucleotide would be added to each well of immobilised RNA. This would drive the hybridisation equilibrium in favour of hybridisation, thus significant hybridisation might occur. Once however the unbound oligonucleotide is washed away, the equilibrium shifts dramatically in favour of dissociation of hybridised probe. Various measures can be taken to increase the 'on-time' of bound oligonucleotides by increasing the binding energy of the interactions. Similar considerations about non-natural nucleic acid analogs as discussed in the first embodiment above apply here. One might conceivably also include cross-linking effectors at this stage that are photo-activatable to ensure that hybridised probe is 'fixed'.

Using libraries of short ON probes is a problem in that to get decent hybridisation one needs a nucleic acid of reasonable length, but each additional base added to a probe increases the number of ONs in a library exponentially. One can overcome the problem of weak hybridisation of short oligonucleotides indirectly by constructing oligonucleotides in sets such that each set is composed of a fixed number of bases of known sequence flanked on one side or other or both by a further fixed number of bases where all possible combinations of nucleotides are represented, these could also be a universal base:

5'-NNXXXXNN-3'

The above example has 2 bases, labeled N for any base, flanking the known sequence 'window', XXXX, on both sides. Thus there would be 256 different sets of 8 mers which could be used to probe the immobilised RNA. This is effectively the same as probing with 4-mers but the flanking bases would increase the stability of interactions. In conjunction with non-natural nucleic acid analogs, this alternative could increase the stability of complexes sufficiently to allow washing and quantitative measurements to be made.

Using probes with windows as short as 4mers might be problematic in that they may appear too frequently in an RNA and thus might make resolving kinetic data more difficult, as there are likely to be more than 2 occurrences of any given 4mer present in a single RNA. Using 5-mers or 6-mers as windows, with stabilising flanking regions, might be easier to resolve, if automated systems were available to cope with the added labour as these are more likely to appear only once in any given RNA.

Probe Arrays

One can test oligonucleotides (ONs) individually by spatially isolating probes in separate wells on a microwell plate. One can immobilise a target RNA and challenge the RNA with individual, fluorescently labeled ONs. Thus for a library of ONs of 4 nt, an array of 256 wells would be required, into which equal quantities of RNA would be immobilised. Each well would be challenged with a different labeled ON. The ON is allowed to hybridise for a predetermined length of time and the unhybridised ONs can then be washed off The quantity of ON hybridised is determined by measuring the fluorescence in each well. This approach will require significant quantities of RNA which can readily be generated using, for example, the T7 phage RNA polymerase system. An alternative is to immobilise the ON probes and challenge these with labeled RNA.

A random oligonucleotide library can be constructed while immobilised on a glass surface such that distinct regions of the array carry distinct oligonucleotides within the library (2). A random library of ONs of 8 nt will have $4^8$ possible members if all possible sequences are represented. Since the ONs are all immobilised on the array there will be no cross-hybridisation.

An RNA for which the tertiary structure is unknown can be cloned and produced in quantity in vitro using for example the T7 phage RNA polymerase system. The RNA can be labeled with a fluorescent label. This can then be used to challenge the immobilised library under conditions that favour the adoption of the normal tertiary structure of the RNA, i.e. in vivo cytoplasmic conditions. The RNA is allowed to hybridise onto the array for a predetermined duration and then unhybridis ed RNAs are washed off. Where hybridisation has occurred can be visualised by detecting fluorescence. The regions of the array from which fluorescence is detected will reveal which ONs the RNA will hybridise to.

These approaches face the problem of weak hybridisation of short ON probe; the minimum size of probe ON will be determined by the strength of interaction necessary to immobilise a large molecule of RNA to the array and allow the RNA to resist being washed off. This would have to be tested empirically but the problem of rapid dissociation should be less severe, when the RNA is the mobile element, as the size of the molecule ought to make it somewhat more sluggish than the small ONs used in the first embodiment. The same approach of creating ONs with short windows of known sequence and flanking regions of random sequence can be readily applied to this embodiment and similar considerations regarding non-natural nucleic acid analogues apply too. Using nuclease resistant analogues would have the additional advantage of being more reusable than phosphodiester linkages, as one can never completely ensure that there is no contamination by nucleases, etc. which would damage a DNA array.

This embodiment is quantitative, as well, as long as each RNA molecule bears a single fluorescent tag. Thus the regions of the array which give the most fluorescence will be those to which the RNA will hybridise to the most strongly. By repeatedly challenging the array with the target RNA for varying but predetermined durations, one would be able to get detailed kinetic information about the hybridisation reaction occurring at each point on the array. This will reveal regions whose structure must be disrupted to allow hybridisation as these will have much slower kinetics.

An alternative to the use of fluorescent labels would be the use of mass labels cleavably linked to the RNA used to probe the array. Mass labels that are derivatives of photo-excitable compounds of the kind discussed in GB 9700746.2, such as nicotinic, sinapinic or cinnamic acid, can be photocleaved and excited into the gas phase by application of appropriate frequencies of light, ideally using a laser. Such labels could be incorporated into an RNA molecule using a terminal transferase reaction for example or an end ligation. If an RNA molecule labelled with laser excitable mass labels of this kind were hybridised to an array of oligonucleotide probes, the degree of hybridisation of the RNA to distinct regions of the array, corresponding to individual oligonucleotides, could be determined by MALDI (Matrix Assisted Laser Desorption Ionisation) mass spectrometry. Simpler, non-exitable mass labels could also be used. In this embodiment the RNA would be hybridised to an array, and following hybridisation, the supernatent would be removed and the array would be embedded in an excitable agent, of the kinds described above, and ionisation of cleaved labels could be mediated indirectly by excitation of the matrix.

Rational Drug Design with the Process

Tertiary Structure Determination

Secondary structure modelling of nucleic acids is well developed and in conjunction with data from a system like this it should be possible to develop decent models of tertiary structure of a target RNA. This will start to make so-called 'rational' drug design a much more quantitative process. In conjunction with other methods such as NMR, complete structure determination will probably be possible. At the very least, accurate secondary structure predicition should be achieved. Most likely only minimal further information from other methods would be needed to determine a structure for any given RNA.

Databases and Drug Selection

This system will, with use, provide a comprehensive database of information about RNA tertiary structure which will lead to better theoretical models of RNA structure and allow a much more specifically targeted approach to designing effective antisense agents. The evidence of Wagner et al (3) suggests that short oligonucleotides can show specificity for target RNAs. The qualification that must be made to this suggestion is that short ONs would have to be highly structure specific. With a comprehensive database of RNA structures a system like this might actually pinpoint potential drugs directly once it is established what structural features are widespread and which are rare. Directly searching for rare features will thus be possible making choice of drug candidates much simpler.

More General Antisense Targets

This system is not specific to detecting RNAse H sensitive sites and could be used for targeting more general antisense agents at various RNAs in cells. Thus this system has potential for more general applications in developing therapeutic agents and research tools for targeting more general functional RNAs in vivo such as ribosomes, splicing apparatus and some of the active RNAs that have recently been implicated in sex determination.

Automation

Both embodiments can be implemented with automated liquid handling systems as the procedure is simple and repetitive. The hybridisation array approach would probably be cheaper in terms of reagents but may be difficult to implement if the binding strength of the interaction between array and target RNA is too small to permit washing of the array. The first embodiment will have a much larger requirement for reagents, although micro-arrays of wells can be constructed to reduce this requirement.

REFERENCES (1) R. K. Mishra, J. J. Toulmé, C.R.Acad. Sci. Paris, Life Sciences 317, 977–982, 1994.
(2) W. Bains, Chemistry in Britain, February 1995, 122–125.
(3) R. W. Wagner et al, Nature Biotechnology 14, 840–844, 1996.
(4) Siew Peng Ho et al, Nucleic Acids Research 24, 1901–1907.

EXAMPLE

Hybridisation of 4-mer Oligonucleotides to 2 TNFα cDNA Subfragments

Subcloning of the TNFα cDNA Clone

Clone number 53007 (pAW731), containing the full length cDNA sequence for TNFa in the vector pFC54.t, was bought from the American Type Culture Collection (ATCC), Rockville, Md., USA. The freeze dried bacteria were resuspended in 2 ml of LB broth and 100 ul was spread onto LB agar plate containing 100 ug/ml of ampicillin. The plates were then incubated at 30° C. overnight. A single colony from the plate was then used to inoculate 100 ml of LB broth containing 100 ug/ml of ampicillin and this was incubated at 30° C., shaking at 225 rpm overnight. Following this the bacterial culture was pelleted by spinning the solution at 5300 rpm in a Hereaus 17RS centrifuge for 15 minutes. The plasmid was then extracted using the Qiaprep Midi Plasmid Purification Kit (Qiagen Ltd.) according to the manufacturers instructions. 2 ul of plasmid was then digested with 10 units of BamHl and Hind III (Boehringer Mannheim) and 2 ul of plasmid digested with 10 units of Hind III in 20 ul at 37° C. for 2 hours. Digestion with BamH1 and Hind III releases the TNFa insert (ATCC). The digested plasmids were then run on a 1% agarose gel. The Hind III digest released a band approximately 700 bp in size and the BamH1 and Hind III digested released a band approximately 700 bp and a band approximately 800 bp in size. The 700 bp fragment was released by Hind III, corresponds to the 3' end of the TNFa insert, and the 800 bp fragment released by Hind III and BamH1, which corresponds to the 5' end of the TNFa insert. These two bands were then cut out of the gel with sterile scalpel blades and spun through GenElute Agarose Spin Columns (Supelco, USA) according to the manufacturers instructions to extract the DNA. The DNA was the precipitated with 2.5 volumes of 100% ethanol and 0.1 volumes of 3M sodium acetate. The solution was then incubated at −20° C. for 30 minutes and then spun at 13000 rpm in a Heraeus A13 benchtop centrifuge for 15 minutes to precipitate the DNA. The supernatant was then poured off and the pellets washed with 100 ul of 70% ethanol and allowed to air dry. The dry pellets were then resuspended in 30 ul of water. 5 ug of plasmid pBluescript SK(+) (Stratagene) was digested with 10 units of BamH1 and Hind III and 5 ug digested with Hind III (Boehringer Mannheim) in 50 ul at 37° C. for 2 hours and then purified with Chromospin-100 columns (Clonetech) according to the manufacturers instructions. The DNA concentration of the purified bands and digested plasmid was measured by reading the absorption at 260 nm and 280 nm in a Pharmacia Genequant spectrophotometer. The 700 and 800 bp bands were then ligated into the appropriately digested pBluescript using 400 units of T4 DNA ligase (New England Biolabs) for the 800 bp fragment and the Rapid Ligation Kit (Boehringer Mannheim) for the 700 bp fragment. 2 ul of each ligation was transformed into 50 ul of XL-1 BLUE competent cells (Stratagene) by incubating the DNA with the cells for 30 minutes on ice, followed by a 45 second 42° C. heat shock and another 2 minutes on ice.

Following this 450 ul of SOC medium was added and the cells incubated at 37° C., shaking at 250 rpm, for 1 hour. 100 ul of the transformation was then plated onto agar plates containing 100 ug/ml ampicillin, 0.1 mM IPTG and 40 ug/ml X-GAL. The plates were then incubated at 37° C. overnight.

White colonies were picked and used to inoculate 2.5ml of LB broth containing 100 ug/ml ampicillin and incubated at 37° C., shaking at 250 rpm, for 7 hours. lml of the bacterial cultures were then spun into eppendorf tubes and the plasmids extracted with the Qiaprep Spin Plasmid Kit (Qiagen). The presence of the correct fragment was checked by digesting 20% of each minipreped plasmid with the appropriate enzyme(s) and the running on an agarose gel. The remaining bacterial cultures from a plasmid containing the 700 bp fragment and from a plasmid containing the 800 bp fragment were then each used to inoculate 250 ml of LB broth containing 100 ug/ml ampicillin which was then incubated at 37° C., shaking at 250 rpm, overnight. Following this the bacterial culture were pelleted by spinning the solutions at 5300 rpm in a Hereaus 17RS centrifuge for 15 minutes. The plasmids were then extracted using the Qiaprep Midi Plasmid Purification Kit (Qiagen Ltd.) according to the manufacturers instructions.

In vitro Transcription 25 ug of each plasmid was linearised by digesting them with 50 units of Cla I in 50 ul of 1×buffer H (Boehringer Mannheim) for 3 hours at 37° C.

The digested plasmids were then purified with Chromospin-100 columns (Clonetech) according to manufacturers instructions.

40 ul of each plasmid was then used to set up a 200 ul in vitro transcription reaction using the RiboMax Large Scale T3 RNA production system (Promega) according to manufacturer's instructions. The remaining 10 ul of each plasmid was then used to set up a 50 ul in vitro transcription reaction using the RiboMax Large Scale T3 RNA production system (Promega) according to manufacturer's instructions but this time 0.25ul of Fluoroscein-12-UTP (Boehringer Mannheim) was included in to each reaction to fluorescently label the RNA. All in vitro transcription reactions were incubated at 37° C. for 3 hours.

Demonstration that RNA Can by Captured Via a Biotinylated Oligo

A 3' biotinylated oligo (cap 53B), with sequence 5'CCACTAGTTCTAGAGCGGCCGCCACCGCGG3' biotin, which would be complementary to the 5' terminus of the RNA produced from the T3 RNA promoter of pBluescript SK (+) and a 5' biotinylated oligo (cap 35B ), with sequence 5' biotin-CCCCCCCTCGAGGTCGACGGTATCGATAAG3' were immobilised to the wells of a black, streptavidin coated microtitre plate (Boehringer Mannheim).

This was achieved by hybridising 200 pmol of each oligo in 50 ul of 10×SSC at room temperature for 1 hour. Each well was then washed twice with 100 ul of 10×SSC. The Fluorescein labelled RNA produced from the 700 and 800 bp fragments were then denatured by heated at 65° C. for 5 minutes. One sixth of each of the RNAs, in 50 ul of 10×SSC, were then added to a well containing cap 35B and cap 53B. The RNAs were then incubated on ice for 30 minutes to allow the RNA to hybridise to the oligos. The wells were then washed 3 times with 100 ul of 10×SSC and the fluorescence measured with a Biolumin 960 (Molecular Dynamics) using Xperiment 1.1.0 software.

The wells were then washed 3 times with 100 ul of 5×SSC, 3 times with 100 ul of 0.1×SSC and the fluorescence measured as before after the 3 washes with 5×SSC and 0.1×SSC.

Readings are in Relative Fluoresent Units with background subtraction.

|  | 10×SSC | 5×SSC | 0.1×SSC |
| --- | --- | --- | --- |
| cap 35B: | | | |
| 800bp fragment | 66974 | 220 | 0 |
| 700bp fragment | 44350 | 133 | 0 |
| cap 53B: | | | |
| 800bp fragment | 50734 | 5136 | 686 |
| 700bp fragment | 42660 | 1438 | 217 |

The above data demonstrate that the cap53B oligo immobilised to the microtitre plate can selectively capture RNA produced from the T3 RNA promoter site of pBluescript SK (+). This data also demonstrates that the RNA can be washed of with high stringency washes (e.g. 0.1×SSC).

Capture of RNA by Cap 53B and Probing with 4 Mers 100 ul of 15×SSC containing 200 pmol of cap 53B oligo was transferred to each of 64 wells of a black, streptavidin coated microtitre plate (Boehringer Mannheim) and incubated at room temperature for 2 hours.

The wells were then washed twice with 150 ul of 15×SSC. RNA transcribed from the 700 and 800 bp clone in a 200 ul reaction (see above) was denatured for 2 minutes at 85° C. Both the 700 and 800 bp RNAs (see above for production) were then each sub-divided between 24 wells in 100 ul of 15×SSC with 16 units of ribonuclease inhibitor (Boehringer Mannheim) and left to hybridise on ice for 1 hour. The wells were then washed twice with 150 ul of ice cold 15×SSC. 200 pmol of each 4mer in 100 ul of 15×SSC was added to 4 wells (3 with RNA and one with just cap 53B) for both species of RNA and left to hybridise for 1 hour on ice. Each well was then washed 3 times with 150 ul of ice cold 15×SSC and the fluorescence read as before (see above). The wells were washed again with 150 ul of ice cold 15×SSC and the Fluorescence measured.

Sequence of 4mers (all Fluoroscein labelled) TACT, TACA, TAAA, TGTC, GTCA, ACCA, TGAA, CACG.

All data points are expressed as Relative Fluorescent Units are the mean of the three wells minus the reading obtained from the well without RNA.

| 4-mer | 1st reading | 2nd reading |
| --- | --- | --- |
| For the 800bp fragment: | | |
| TACT | 0 | 655 |
| TACA | 2292 | 562 |
| TAAA | 0 | 0 |
| TGTC | 1118 | 382 |
| GTCA | 498 | 57 |
| ACCA | 0 | 0 |
| TGAA | 0 | 0 |
| CAGG | 0 | 116 |
| For the 700bp fragment: | | |
| TACT | 756 | 135 |
| TACA | 0 | 0 |
| TAAA | 875 | 259 |
| TGTC | 658 | 0 |
| GTCA | 0 | 0 |
| ACCA | 0 | 0 |
| TGAA | 536 | 156 |
| CAGG | 0 | 0 |

The above data demonstrate that the 4 mers TACA, TGTC and GTCA hybridise to the RNA transcribed from the 800 bp fragment in descending order of strength. These oligos correspond to the following numbered positions in the primary sequence using the 'A' of the start codon as base 1 in TNFa.

| For the 800bp fragment: | |
| --- | --- |
| TACA | 264–267 |
| | 276–279 |
| | 392–395 |
| TGTC | 60–63 |
| | 256–259 |
| | 770–773 |
| GTCA | 255–258 |
| | 615–618 |

There is an obvious clustering of all three oligos, which bind, around bases 250 to 280.

Oligos found in the sequence but did not bind

| | |
|---|---|
| TAAA | 751–754 |
| ACCA | 371–374 |
| | 374–373 |
| | 568–571 |
| CAGG | 114–117 |
| | 147–150 |
| | 262–265 |
| | 336–339 |
| | 390–393 |
| | 527–530 |
| | 566–569 |
| | 696–699 |
| | 737–740 |

For the 700 bp Fragment

The oligos TAAA, TACA and TGAA hybridise to the RNA transcribed from the 700 bp fragment in descending order of strength. These oligos correspond to the following numbered positions in the primary sequence using the 'A' of the start codon as base 1 in TNFa.

| | |
|---|---|
| TAAA | 838–841 |
| | 1146–1149 |
| | 1168–1171 |
| | 1175–1178 |
| | 1179–1182 |
| | 1186–1189 |
| | 1190–1193 |
| | 1194–1197 |
| | 1210–1213 |
| | 1351–1356 |
| TGAA | 873–876 |
| | 921–924 |
| | 1461–1464 |

TACA is found within the T3 RNA promoter site of pBluescript SK(+).

Oligos found in the sequence but did bind

| | |
|---|---|
| TACA | 1206–1209 |
| | 1246–1249 |
| | 1313–1316 |
| | 1449–1452 |
| TGTC | 970–973 |
| | 1051–1054 |
| | 1105–1108 |
| | 1267–1270 |
| GTCA | 969–972 |
| | 1050–1053 |
| | 1398–1401 |
| ACCA | 1001–1004 |
| | 1395–1398 |
| CAGG | 866–869 |
| | 888–891 |
| | 967–970 |
| | 1232–1235 |
| | 1321–1324 |

The fact that different sets of 4mers hybridise to the 2 different RNA species provides evidence that the signal obtain is the product of true hybridisation and not due to a non-specific binding property of the particular 4mers. This is backed up further by the fact that a 4 mer with a 100% AT content, and hence lowest Tm, has hybridised while a 4 mer with a 75%GC content, and therefore a much greater Tm, has not hybridised.

Also, all the oligo sequences are found in both RNA species but only a selection of the oligos were able to bind, and in one instance clustered around a particular sequence. This clustering of 4-mers suggests that this section of the RNA is single stranded or is accessible and is, therefore, an obvious target for antisense.

Therefore, this experiment provides evidence that the single strand parts of an RNA molecule can be probed, and sequence information obtained, by the hybridisation of a 4mer.

What is claimed is:

1. A method for identifying an antisense oligonucleotide capable of binding to a target mRNA, comprising:
   (a) contacting the target mRNA with each member of an oligonucleotide library separately under hybridization conditions,
      wherein each member of the oligonucleotide library consists essentially of a set of oligonucleotides, each oligonucleotide comprising a central known sequence flanked on both sides by one or more flanking bases, wherein the central known sequence consists of a first fixed number of four or five bases of known sequence, the flanking bases consist of a second fixed number of between 2 and 8 bases, and the oligonucleotides are a common length of no more than 12 bases, and wherein the oligonucleotides of a set comprise all possible combinations of the flanking bases, and wherein each member of the oligonucleotide library comprises a different central known sequence and all possible combinations of central known sequence are present in the oligonucleotide library;
   (b) optionally removing unhybridized material;
   (c) determining which member or members hybridize; and
   (d) comparing the known sequence of each member which hybridizes with the known sequence of the target mRNA so as to identify in the target MRNA one or more antisense binding sites.

2. A method according to claim 1, wherein each member of the oligonucleotide library is contacted with the target mRNA in a separate container.

3. A method according to claim 2, wherein the target mRNA is immobilized in the container.

4. A method according to claim 1, wherein each member of the oligonucleotide library is immobilized at a separate location on a hybridization array.

5. A method according to claim 1, wherein the common length of the oligonucleotides is no more than ten bases.

6. A method according to claim 1, wherein the step of determining which member or members hybridize comprises determining the member or members which hybridize more rapidly.

7. A method according to claim 1, wherein the oligonucleotides comprise DNA analogues.

8. A method according to claim 1, wherein the target mRNA or the members of the oligonucleotide library are labeled with a label and hybridization is determined by detection of the label.

9. A method according to claim 8, wherein the label comprises a fluorescent label or a mass label.

10. A method according to claim 8, wherein a detection surface is used to detect the proximity of the label thereto.

11. A method according to claim 8, wherein the label comprises a radiolabel and the detection surface comprises a scintillant.

* * * * *